US008012077B2

(12) United States Patent
Hoeppner

(10) Patent No.: US 8,012,077 B2
(45) Date of Patent: Sep. 6, 2011

(54) BLOOD SEPARATING DEVICE

(75) Inventor: Jacy C. Hoeppner, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 681 days.

(21) Appl. No.: 12/126,028

(22) Filed: May 23, 2008

(65) Prior Publication Data

US 2009/0289014 A1 Nov. 26, 2009

(51) Int. Cl.
*B01D 21/26* (2006.01)
(52) U.S. Cl. ................. 494/37; 494/3; 494/43; 494/47; 494/63; 210/740
(58) Field of Classification Search .................... 210/90, 210/740, 741, 782; 410/3, 37, 43, 47, 48, 410/63
See application file for complete search history.

(56) References Cited

U.S. PATENT DOCUMENTS

| | | |
|---|---|---|
| 2,553,004 A | 5/1951 | Rabatine |
| 3,141,846 A | 7/1964 | Laven, Jr. |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,593,915 A | 7/1971 | Steinacker |
| 3,647,070 A | 3/1972 | Adler |
| 3,779,383 A | 12/1973 | Ayres |
| 3,785,549 A | 1/1974 | Latham, Jr. |
| 3,814,248 A | 6/1974 | Lawhead |
| 3,850,369 A | 11/1974 | Bull et al. |

(Continued)

FOREIGN PATENT DOCUMENTS

AU 696278 1/1999

(Continued)

OTHER PUBLICATIONS

Office Action mailed Sep. 14, 2010 for Japanese Application No. 2007-554193 filed Aug. 23, 2007 has been provided including a partial translation thereof. Japanese Application No. 2007-554193 claims benefit of PCT/US2006/003599, filed Jan. 30, 2006; claiming priority from U.S. Appl. Nos. 60/651,050, filed Feb. 7, 2005; 60/654,718, filed Feb. 17, 2005; and 60/723,312, filed Oct. 04, 2005 of which U.S. Appl. No. 11/831,605 filed Jul. 31, 2007, and U.S. Appl. No. 12/772,497 filed May 3, 2010 claim benefit.

(Continued)

*Primary Examiner* — Walter D Griffin
*Assistant Examiner* — Timothy Cleveland
(74) *Attorney, Agent, or Firm* — Harness, Dickey

(57) ABSTRACT

A device for separating components of a composition according to density. The device includes a rotatable chamber and a plurality of buoys. The rotatable chamber has an axis of rotation. The plurality of buoys are positioned within the rotatable chamber and about the axis of rotation. The buoys are radially movable between an expanded position in which the buoys are at a first location relative to the axis of rotation and a contracted position in which the buoys are at a second location relative to the axis of rotation. The first location is further from the axis of rotation than the second location is. The buoys are movable in response to force generated during rotation of the rotatable chamber.

36 Claims, 9 Drawing Sheets

U.S. PATENT DOCUMENTS

| | | |
|---|---|---|
| 3,879,295 A | 4/1975 | Glover et al. |
| 3,894,952 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,941,699 A | 3/1976 | Ayres |
| 3,972,812 A | 8/1976 | Gresl, Jr. |
| 3,982,691 A | 9/1976 | Schlutz |
| 4,001,122 A | 1/1977 | Griffin |
| 4,046,699 A | 9/1977 | Zine, Jr. |
| 4,055,501 A | 10/1977 | Cornell |
| 4,059,108 A | 11/1977 | Latham, Jr. |
| 4,077,396 A | 3/1978 | Wardlaw et al. |
| 4,152,270 A | 5/1979 | Cornell |
| 4,159,896 A | 7/1979 | Levine et al. |
| 4,187,979 A | 2/1980 | Cullis et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies et al. |
| 4,377,572 A | 3/1983 | Schwarz et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al. |
| 4,446,021 A | 5/1984 | Aufderhaar et al. |
| 4,453,939 A | 6/1984 | Zimmerman et al. |
| 4,464,167 A | 8/1984 | Schoendorfer et al. |
| 4,537,767 A | 8/1985 | Rothman et al. |
| RE32,089 E | 3/1986 | Blatt et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,974 A | 7/1989 | Kelley et al. |
| 4,853,137 A | 8/1989 | Ersson |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer et al. |
| 4,902,281 A | 2/1990 | Avoy |
| 4,928,603 A | 5/1990 | Rose et al. |
| 4,929,242 A | 5/1990 | Desecki et al. |
| 4,933,291 A | 6/1990 | Daiss et al. |
| 4,943,273 A | 7/1990 | Pages et al. |
| 4,946,601 A | 8/1990 | Fiehler |
| 4,950,220 A | 8/1990 | Wells et al. |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,030,215 A | 7/1991 | Morse et al. |
| 5,030,341 A | 7/1991 | McEwen et al. |
| 5,045,048 A | 9/1991 | Kaleskas et al. |
| 5,053,127 A | 10/1991 | Schoendorfer et al. |
| 5,071,570 A | 12/1991 | Shiraki et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,204,537 A | 4/1993 | Bennet et al. |
| 5,206,023 A | 4/1993 | Hunziker et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,234,608 A | 8/1993 | Duff |
| 5,236,604 A | 8/1993 | Fiehler |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,370,802 A | 12/1994 | Brown |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,484,383 A | 1/1996 | Fitch, Jr. et al. |

| | | | | | | |
|---|---|---|---|---|---|---|
| 5,494,578 | A | 2/1996 | Brown et al. | 2005/0084961 A1 | 4/2005 | Hedrick et al. |
| 5,494,592 | A | 2/1996 | Latham, Jr. et al. | 2005/0109716 A1 | 5/2005 | Leach et al. |
| 5,505,685 | A | 4/1996 | Antwiler | 2005/0153441 A1 | 7/2005 | Hedrick et al. |
| 5,510,102 | A | 4/1996 | Cochrum | 2005/0153442 A1 | 7/2005 | Katz et al. |
| 5,533,518 | A | 7/1996 | Vogler | 2005/0196874 A1 | 9/2005 | Dorian et al. |
| 5,560,830 | A | 10/1996 | Coleman et al. | 2005/0247715 A1 | 11/2005 | Ellsworth et al. |
| 5,577,513 | A | 11/1996 | Van Vlasselaer | 2005/0260174 A1 | 11/2005 | Fraser et al. |
| 5,585,007 | A | 12/1996 | Antanavich et al. | 2005/0260175 A1 | 11/2005 | Hedrick et al. |
| 5,589,462 | A | 12/1996 | Patat et al. | 2005/0282275 A1 | 12/2005 | Katz et al. |
| 5,601,727 | A | 2/1997 | Bormann et al. | 2006/0083720 A1 | 4/2006 | Fraser et al. |
| 5,607,579 | A | 3/1997 | Latham, Jr. et al. | 2006/0175242 A1 | 8/2006 | Dorian et al. |
| 5,614,106 | A | 3/1997 | Payrat et al. | 2006/0175244 A1 | 8/2006 | Dorian et al. |
| 5,632,905 | A | 5/1997 | Haynes | 2006/0196885 A1 | 9/2006 | Leach et al. |
| 5,641,622 | A | 6/1997 | Lake et al. | 2006/0243676 A1 | 11/2006 | Swift et al. |
| 5,643,192 | A | 7/1997 | Hirsh et al. | 2007/0036768 A1 | 2/2007 | Fraser et al. |
| 5,643,193 | A | 7/1997 | Papillon et al. | 2007/0075016 A1 | 4/2007 | Leach |
| 5,674,173 | A | 10/1997 | Hlavinka et al. | 2008/0011684 A1 | 1/2008 | Dorian et al. |
| 5,733,545 | A | 3/1998 | Hood, III | 2008/0283474 A1 | 11/2008 | Leach et al. |
| 5,736,033 | A | 4/1998 | Coleman et al. | 2010/0206798 A1 | 8/2010 | Dorian et al. |
| 5,788,662 | A | 8/1998 | Antanavich et al. | 2010/0226909 A1 | 9/2010 | Hecker et al. |
| 5,795,489 | A | 8/1998 | Holm et al. | | | |
| 5,795,571 | A | 8/1998 | Cederholm-Williams et al. | FOREIGN PATENT DOCUMENTS | | |
| 5,853,600 | A | 12/1998 | McNeal et al. | BR | 9103724 | 3/1993 |
| 5,860,937 | A | 1/1999 | Cohen | CA | 1321138 | 8/1993 |
| 5,889,584 | A | 3/1999 | Wardlaw | CA | 2182862 | 6/1996 |
| 5,918,622 | A | 7/1999 | Perez et al. | CN | 1074709 | 7/1993 |
| 5,924,972 | A | 7/1999 | Turvaville et al. | DE | 56103 | 10/1860 |
| 5,934,803 | A | 8/1999 | Hutter | DE | 1443359 | 11/1968 |
| 5,980,757 | A | 11/1999 | Brown et al. | DE | 4202667 | 5/1993 |
| 6,011,490 | A | 1/2000 | Tonnesen et al. | EP | 090997 | 10/1983 |
| 6,022,306 | A | 2/2000 | Dumont et al. | EP | 0102773 | 3/1984 |
| 6,025,201 | A | 2/2000 | Zelmanovic et al. | EP | 0109374 | 5/1984 |
| 6,051,146 | A | 4/2000 | Green et al. | EP | 0142339 | 5/1985 |
| 6,053,856 | A | 4/2000 | Hlavinka | EP | 0253198 | 1/1988 |
| 6,054,122 | A | 4/2000 | MacPhee et al. | EP | 0272915 A2 | 6/1988 |
| 6,063,297 | A | 5/2000 | Antanavich et al. | EP | 285891 | 10/1988 |
| 6,071,423 | A | 6/2000 | Brown et al. | EP | 0295771 | 12/1988 |
| 6,090,793 | A | 7/2000 | Zimmermann et al. | EP | 0417818 | 3/1991 |
| 6,096,309 | A | 8/2000 | Prior et al. | EP | 0534178 | 3/1993 |
| 6,102,843 | A | 8/2000 | Kelley et al. | EP | 0592242 | 4/1994 |
| 6,117,425 | A | 9/2000 | MacPhee et al. | EP | 1005910 | 6/2000 |
| 6,153,113 | A | 11/2000 | Goodrich et al. | EP | 1427279 A1 | 6/2004 |
| 6,196,987 | B1 | 3/2001 | Holmes et al. | EP | 1467746 A2 | 10/2004 |
| 6,197,325 | B1 | 3/2001 | MacPhee et al. | EP | 1670315 A2 | 6/2006 |
| 6,200,287 | B1 | 3/2001 | Keller et al. | EP | 1716901 A1 | 11/2006 |
| 6,214,338 | B1 | 4/2001 | Antanavich et al. | GB | 854715 | 11/1960 |
| 6,245,900 | B1 | 6/2001 | Yamasaki et al. | JP | 60-053845 | 3/1985 |
| 6,277,961 | B1 | 8/2001 | Hock et al. | JP | 60250014 A | 12/1985 |
| 6,280,400 | B1 | 8/2001 | Niermann | JP | 63182055 A | 7/1988 |
| 6,296,602 | B1 | 10/2001 | Headley | JP | 6454256 | 4/1989 |
| 6,316,247 | B1 | 11/2001 | Katz et al. | JP | 2036872 | 2/1990 |
| 6,322,785 | B1 | 11/2001 | Landesberg et al. | JP | 02071747 | 3/1990 |
| 6,334,842 | B1 | 1/2002 | Hlavinka et al. | JP | 04500170 T | 1/1992 |
| 6,342,157 | B1 | 1/2002 | Hood, III | JP | 6250014 | 9/1994 |
| 6,368,298 | B1 | 4/2002 | Beretta et al. | JP | 09187504 A | 7/1997 |
| 6,464,624 | B2 | 10/2002 | Pages | JP | 9509432 T | 9/1997 |
| 6,472,162 | B1 | 10/2002 | Coelho et al. | JP | 11502502 T | 3/1999 |
| 6,516,953 | B1 | 2/2003 | DiCesare et al. | JP | 2000117150 A | 4/2000 |
| 6,544,162 | B1 | 4/2003 | Van Wie et al. | JP | 02129224 | 10/2000 |
| 6,563,953 | B2 | 5/2003 | Lin et al. | JP | 2001017540 A | 1/2001 |
| 6,629,919 | B2 | 10/2003 | Egozy et al. | JP | 2005523128 T | 8/2005 |
| 6,676,629 | B2 | 1/2004 | Andrew et al. | MX | 246078 | 5/2007 |
| 6,758,978 | B1 | 7/2004 | Bedell | WO | WO-8400905 | 3/1984 |
| 6,764,531 | B2 | 7/2004 | Hogan | WO | WO-8802259 | 4/1988 |
| 6,777,231 | B1 | 8/2004 | Katz et al. | WO | WO-8901827 A1 | 3/1989 |
| 6,905,612 | B2 | 6/2005 | Dorian et al. | WO | WO-9010031 | 9/1990 |
| 6,979,307 | B2 | 12/2005 | Beretta et al. | WO | WO-9222312 | 12/1992 |
| 7,011,644 | B1 | 3/2006 | Andrew et al. | WO | WO-9305067 | 3/1993 |
| 7,077,273 | B2 | 7/2006 | Ellsworth et al. | WO | WO-9308904 | 5/1993 |
| 7,179,391 | B2 | 2/2007 | Leach et al. | WO | WO-9407548 | 4/1994 |
| 2002/0032112 A1 | | 3/2002 | Pages | WO | WO-9616714 A1 | 6/1996 |
| 2002/0076400 A1 | | 6/2002 | Katz et al. | WO | WO-9617871 | 6/1996 |
| 2003/0082152 A1 | | 5/2003 | Hedrick et al. | WO | WO-9848938 | 11/1998 |
| 2003/0191429 A1 | | 10/2003 | Andrew et al. | WO | WO-0103756 | 1/2001 |
| 2004/0171146 A1 | | 9/2004 | Katz et al. | WO | WO-0183068 | 11/2001 |
| 2004/0182788 A1 | | 9/2004 | Dorian et al. | WO | WO-0224107 | 3/2002 |
| 2004/0182795 A1 | | 9/2004 | Dorian et al. | WO | WO-03015800 | 2/2003 |
| 2004/0251217 A1* | | 12/2004 | Leach et al. ............ 494/37 | WO | WO-03024215 A1 | 3/2003 |
| 2005/0076396 A1 | | 4/2005 | Katz et al. | WO | WO-03053362 A2 | 7/2003 |

| | | |
|---|---|---|
| WO | WO-03090839 A1 | 11/2003 |
| WO | WO-03092894 A2 | 11/2003 |
| WO | WO-2004009207 | 1/2004 |
| WO | WO-2004037427 A1 | 5/2004 |
| WO | WO-2004104553 A2 | 12/2004 |
| WO | WO-2005034843 A2 | 4/2005 |
| WO | WO-2006081699 A1 | 8/2006 |
| WO | WO-2007142908 A1 | 12/2007 |

OTHER PUBLICATIONS

Office Action mailed Sep. 14, 2010 for Japanese Application No. 2007554191 filed Aug. 7, 2007 has been provided including a partial translation thereof. Japanese Application No. 2007554191 claims benefit of PCT/US2006/003597, filed Jan. 30, 2006; claiming priority from U.S. Appl. Nos. 60/651,050, filed Feb. 7, 2005; 60/654,718, filed Feb. 17, 2005; and 60/723,312, filed Oct. 4, 2005 of which U.S. Appl. No. 11/831,605 filed Jul. 31, 2007 and U.S. Appl. No. 12/772,497 filed May 3, 2010 claim benefit.
International Preliminary Report on Patentability mailed Feb. 12, 2009, for PCT/US2007/017055 filed Jul. 31, 2007, which claims benefit of U.S. Appl. No. 60/834,550, filed Jul. 31, 2006, based on U.S. Appl. No. 60/723,312, filed Oct. 4, 2005; U.S. Appl. No. 60/654,718, filed Feb. 17, 2005; and U.S. Appl. No. 60/651,050, filed Feb. 7, 2005.
International Preliminary Examination Report and Written Opinion issued Aug. 31, 2010 for PCT/US2009/035564 claiming benefit of U.S. Appl. No. 61/078,178, filed Jul. 3, 2008 of which U.S. Appl. No. 12/395,085, filed Feb. 27, 2009 claims benefit.
Office Action mailed Apr. 6, 2010 for Japanese Application No. 2007-554193 filed Aug. 23, 2007 has been provided including a partial translation thereof, which cites JP11-502502 and JP2001017540. Japanese Application No. 2007-554193 claims benefit of PCT/US2006/003599, filed Jan. 30, 2006; claiming priority from U.S. Appl. Nos. 60/651,050, filed Feb. 7, 2005; 60/654,718, filed Feb. 17, 2005; and 60/723,312, filed Oct. 4, 2005 of which U.S. Appl. No. 11/831,605 filed Jul. 31, 2007 and U.S. Appl. No. 12/772,497 filed May 3, 2010 claim benefit.
Office Action mailed Apr. 6, 2010 for Japanese Application No. 2007554191 filed Aug. 7, 2007 has been provided including a partial translation thereof, which also cites JP2001017540. Japanese Application No. 2007554191 claims benefit of PCT/US2006/003597, filed Jan. 30, 2006; claiming priority from U.S. Appl. Nos. 60/651,050, filed Feb. 7, 2005; 60/654,718, filed Feb. 17, 2005; and 60/723,312, filed Oct. 4, 2005 of which U.S. Appl. No. 11/831,605 filed Jul. 31, 2007 and U.S. Appl. No. 12/772,497 filed May 3, 2010 claim benefit.
International Search Report and Written Opinion mailed Aug. 12, 2008 for PCT/US07/17055.
Anesthesiology, vol. 81, No. 4, pp. 1074-1077, Oct. 1994, Hiromasa Mitsuhata, M.D., et al., "An Anaphylactic Reaction to Topical Fibrin Glue".
Ann Thorac Surg, vol. 53, pp. 530-531, 1992, Mehmet C. Oz, M.D., et al., "Autologous Fibrin Glue From Intraoperatively Collected Platelet-Rich Plasma".
Ann Thorac Surg, vol. 56, pp. 387-389, 1993, Robert L. Quigley, M.D., et al., "Intraoperative Procurement of Autologous Fibrin Glue".
Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31 (3 1991): 408-11.
Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac Cardiovasc Surg* 105 (5 1993): 892-7.
Biopolymers, vol. 27, pp. 763-774, 1988, Gerald Marx, "Mechanism of Fibrin Coagulation Based on Selective, Cation-Driven, Protofibral Association".
Casali, B., F. Rodeghiero, A. Tosetto, B. Palmieri, R. Immovilli, C. Ghedini, and P. Rivasi. "Fibrin glue from single-donation autologous plasmapheresis." Transfusion 32 (Jul. 1992): 641-3.

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 (May), 1976.
DelRossi, A. J., A. C. Cernaianu, R. A. Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100 (2 1990): 281-6.
Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".
Edlich, Richard F., George T. Rodeheaver, and John G. Thacker. "Surgical Devices in Wound Healing Management." In *Wound Healing: Biochemical & Clinical Aspects*,ed. I. Kelman Cohen, Robert F. Diegelmann, and William J. Lindblad. 581-600. 1st ed., Vol. Philadelphia: W.B. Saunders Company, 1992).
Epstein, G. H., R. A. Weisman, S. Zwillenberg, and A. D. Schreiber. "A new autologous fibrinogen-based adhesive for otologic surgery." *Ann Otol Rhinol Laryngol* 95 (1 Pt 1 1986): 40-5.
First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (15 1975): 495-501.
Gibble, J. W. and P. M. Ness. "Fibrin glue: the perfect operative sealant?" *Transfusion* 30 (8 1990): 741-7.
Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.
Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (3 1992): 357-9.
Hennis, H. L., W. C. Stewart, and E. K. Jeter. "Infectious disease risks of fibrin glue [letter]." *Ophthalmic Surg* 23 (9 1992): 640.
Jackson, C. M. and Y. Nemerson. "Blood coagulation." *Annu Rev Biochem* 49 (811 1980): 765-811.
Journal of Biomaterials Applications, vol. 7, pp. 309-353, Apr. 1993, David H. Sierra, "Fibrin Sealant Adhesive Systems: A review of their Chemistry, Material Properties and Clinical Appllications".
Journal of Oral Maxillofacial Surgery, vol. 43, pp. 605-611, 1985, Helene Matras, M.D., "Fibrin Seal: The State of the Art".
Kjaergard, H. K,, U. S. Weis-Fogh, H. Sorensen, J. Thiis, and I. Rygg. "A simple method of preparation of autologous fibrin glue by means of ethanol." *Surg Gynecol Obstet* 175 (1 1992): 72-3.
Kjaergard, H. K., Fogh Us Weis, and J. J. Thiis. "Preparation of autologous fibrin glue from pericardial blood." *Ann Thorac* Sur 55 (2 1993): 543-4.
Laryngoscope vol. 99, pp. 974-976, Sep. 1989, Kyosti Laitakari, M.D., et al., "Autologous and Homologous Fibrinogen Sealants: Adhesive Strength".
Laryngoscope, vol. 95, pp. 1074-1076, Sep. 1985, Karl H. Siedentop, M.D., et al., "Autologous Fibrin Tissue Adhesive".
Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".
Lerner, R. and N. S. Binur. "Current status of surgical adhesives." J Surg Res 48 (2 1990): 165-81.
Matras, Helene, H. P. Dinges, H. Lassmann, and B. Mamoli. "Zur nahtlosen interfaszikularen Nerventransplantation im Tierexperinnent." Wein Med Woschtr 122 (37 1972): 517-523.
Moretz, W., Jr., J Shea Jr., J. R. Emmett, and J Shea. "A simple autologous fibrinogen glue for otologic surgery." *Otolaryngol Head Neck Surg* 95 (1 1986): 122-4.
Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".
Sanal, M. "Does fibrin glue cause foreign body reactions? [letter]." *Eur J Pediatr Surg* 3 (3 1993): 190 (1 page).
Sanal, M., H. Dogruyol, A. Gurpinar, and O. Yerci. "Does fibrin glue cause foreign body reactions?" *Eu r J Pediatr Surg* 2 (5 1992): 285-6.

The American Journal of Surgery, vol. 168, pp. 120-122, Aug. 1994, Roy L. Tawes, Jr., M.D., et al., "Autologous Fibrin Glue: The Last Step in Operative Hemostatis".

The American Surgeon, vol. 55, pp. 166-168, Mar. 1989, William D. Spotnitz, M.D., et al., "Successful Use of Fibrin Glue During 2 Years of Surgery at a University Medical Center".

Vortech™ Concentration System, "Do you want a sticky gel to improve the handling of your bone graft?, Platelet Rich Plasma Concentrate, High Volume in 5 Minutes," Biomet Biologics, Inc., Aug. 2005.

Vox Sanquinis, vol. 68: 82-89, 02/95, Boomgaard Et. al, Pooled Platelet Concentration Prepred by the . . . .

Weis-Fogh, U. S. "Fibrinogen prepared from small blood samples for autologous use in a tissue adhesive system." Eur Surg Res 20 (5-6 1988): 381-9.

Wiseman, David M., David T. Rovee, and Oscar M. Alverez. "Wound Dressings: Design and Use." In *Wound Healing: Biochemical & Clinical Aspects*,ed. I. Kelman Cohen, Robert F. Diegelmann, and William J. Lindblad. 562-580. 1st ed., Vol. Philadelphia: W. B. Saunders Company, 1992).

International Search Report and Written Opinion for PCT/US2006/003599 mailed Aug. 21, 2006.

International Search Report and Written Opinion for PCT/US2006/003597 mailed Feb. 6, 2006.

"Cell Isolation Techniques, Methods and Materials, Working with Enzymes," (2004) (9 pages) Worthington Biochemical Corp.

"Cell Isolation Theory, Tissue Types," (2004) (5 pages) Worthington Biochemical Corp.

"Cytori Celution Cell Concentrate Device," Exhibit 14, 510(k) Summary, FDA approval K060482 (Sep. 28, 2006).

"Frequently Asked Questions, 1. Kits, 2. Engzymes," (2003) 3 pages Worthington Biochemical Corp.

"Sefar Solutions for the Healthcare Industry," brochure (2003) 9 pages Sefar Medifab®.

"Trypsinization of Adherent Cells," (undated) 2 pages.

DeUgarte, M.D., Daniel A., et al., "Future of Fat as Raw Material for Tissue Regneration," (2007) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Gimble, Jeffrey M., "Adipose-Derived Stem Cells for Regenerative Medicine," Circulation Research (2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

GPS® III System, GPS® III Platelet Separation System, Leadership through Technology, brochure, Jul. 2007 (8 sheets) .

GPS® System, "GPS® Platelet Concentrate System," Cell Factor Technologies, Inc., Biomet Orthopaedics, Inc., (2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS® II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS® II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Guilak, Frank, et al., "Adipose-derived adult stem cells for cartilage tissue engineering," Biorheology 41 (2004) pp. 389-399, IOS Press.

Hattori, et al., "Osteogenic Potential of Human Adipose Tissue-Derived Stromal Cells as an Alternative Stem Cell Source," Cells Tissues Organs (2004) 178:2-12 Karger.

International Search Report and Written Opinion mailed Jul. 3, 2009 for PCT/US2009/035564 claiming benefit of U.S. Appl. No. 61/078,178, filed Jul. 3, 2008.

Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.

Marrowstim™ Concentration System, (2008) 20 pages Biomet Biologics, Inc.

Nakagami, Hironori, et al., "Novel Autologous Cell Tehrapy in Ischemic Limb Disease Through Growth Factor Secretion by Cultured Adipose Tissue-Derived Stromal Cells," Angiogenesis by Adipose Tissue-Derived Cells, (2005) pp. 2542-2547, American Heart Association, Inc.

Nathan, Suresh et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.

Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.

Planat-Bénard, V., et al., "Spontaneous Cardiomyocyte Differentiation From Adipose Tissue Stroma Cells," Adipose-Derived Cell Cardiomyocyte (2004) pp. 223-229 American Heart Association, Inc.

Plasmax™ Plasma Concentrate, brochure (2006) 5 pages Biomet Biologics, Inc.

Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.

Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Pub. 2005) pp. 1409-1422.

Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (2007) pp. 1423-1424.

Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (2007) pp. 818-827 AlphaMed Press.

Sigma-Aldrich® Alkaline Phosphatase (Procedure No. 85), drug fact sheet, (2003) pp. 1-2, Sigma-Aldrich, Inc.

Takahashi, Kazutoshi et al., "Induction of Pluripotent Stem Cells from Adult Human Fibroblasts by Defined Factors," Cell, (2007) pp. 1-12, Elsevier Inc.

Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.

Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.

Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.

\* cited by examiner

BLOOD SEPARATING DEVICE

FIELD

The present disclosure relates to devices and methods for separating blood into its different fractions or parts.

BACKGROUND

The statements in this section merely provide background information related to the present disclosure and may not constitute prior art.

Whole blood includes a variety of different fractions or parts. For example, human whole blood includes platelet rich plasma (PRP), platelet poor plasma (PPP), red blood cells (RBCs), and white blood cells (WBCs). These different blood fractions have a variety of clinical and experimental uses. Thus, there is a need for devices and methods that separate and isolate the different fractions of whole blood, as well as the different components of most any other multi-component composition.

SUMMARY

The present teachings provide for a device for separating components of a composition according to density. The device includes a rotatable chamber and a plurality of buoys. The rotatable chamber has an axis of rotation. The plurality of buoys are positioned within the rotatable chamber and about the axis of rotation. The buoys are radially movable between an expanded position in which the buoys are at a first location relative to the axis of rotation and a contracted position in which the buoys are at a second location relative to the axis of rotation. The first location is further from the axis of rotation than the second location is. The buoys are movable in response to force generated during rotation of the rotatable chamber.

The present teachings further provide for a blood component separation device that includes a rotatable chamber, a plurality of buoys, a first capture area, a second capture area, and a third capture area. The rotatable chamber has an axis of rotation, an inner wall surface, and a floor that is inclined from the axis of rotation to the inner wall surface. The plurality of buoys surround the axis of rotation and are slidable along the floor so as to move radially between an expanded position in which the buoys are distal to the axis of rotation when the chamber is rotating and a contracted position in which the buoys are proximate to the axis of rotation when the chamber is stationary. The buoys have a density that is proximate to the density of platelet rich plasma. The first capture area is between an inner surface of the buoys in the contracted position and the axis of rotation. The first capture area captures platelet poor plasma after blood is spun in the separation device. The second capture area is between an outer surface of the buoys in the contracted position and the inner wall surface of the rotatable chamber. The second capture area captures red blood cells after blood is spun in the separation device. The third capture area is between the first capture area and the second capture area. The third capture area captures platelet rich plasma after blood is spun in the separation device.

The present teachings also provide for a method for separating whole blood into different components. The method includes the following: inserting whole blood into a rotatable chamber of a blood separation device having an axis of rotation and an inner wall surface; rotating the chamber for a sufficient period of time such that components of the whole blood separate according to density; and stopping rotation of the chamber such that the plurality of buoys move from an expanded position in which the buoys are distal to the axis of rotation to a contracted position in which the buoys are proximal to the axis of rotation to isolate red flood cells of the blood between the buoys and the inner wall surface, to isolate platelet poor plasma between the buoys and the axis of rotation, and to isolate platelet rich plasma at a common distance from the axis of rotation as the buoys.

The present teachings provide for a blood component separation device. The device includes a rotatable chamber having an axis of rotation, an inner wall surface, and a floor that is inclined from the axis of rotation to the inner wall surface. The device further includes a plurality of buoys positioned within the rotatable chamber and surrounding the axis of rotation. Each of the buoys have a density that permits the buoys to settle at an interface between red blood cells and a platelet rich plasma buffy coat. Each of the buoys are slidable along the floor so as to move radially between an expanded position in which the buoys are distal to the axis of rotation when the chamber is rotating and a contracted position in which the buoys are proximate to the axis of rotation when the chamber is stationary. Each of the buoys include an arcuate outer surface, an arcuate inner surface, a substantially linear side surface, and a collection trough between the outer surface and the inner surface. The device further includes a collection bowl, a fluid line, a collection basin, a valve, a first capture area, a second capture area, and a third capture area. The collection bowl is at the axis of rotation. The fluid line extends between the collection trough and the collection bowl. The collection basin is attached to a base of the rotatable chamber. The valve is positioned to regulate passage of material between the rotatable chamber and the collection basin. The first capture area is between the inner surfaces of the buoys in the contracted position and the axis of rotation. The first capture area captures platelet poor plasma after blood is spun in the separation device. The second capture area is between the outer surfaces of the buoys in the contracted position and the inner wall surfaces. The second capture area captures red blood cells after blood is spun in the separation device. The third capture area includes the collection troughs. The third capture area captures platelet rich plasma after blood is spun in the separation device.

The present teachings further provide for a method for separating bone marrow aspirate into different components. The method includes inserting bone marrow aspirate into a rotatable chamber of a bone marrow aspirate separation device having an axis of rotation and an inner wall surface; rotating the chamber for a sufficient period of time such that components of the bone marrow aspirate separate according to density; and stopping rotation of the chamber such that the plurality of buoys move from an expanded position in which the buoys are distal to the axis of rotation to a contracted position in which the buoys are proximal to the axis of rotation to isolate red blood cells of the bone marrow aspirate between the buoys and the inner wall surface, to isolate bone marrow plasma between the buoys and the axis of rotation, and to isolate multipotent cells at a common distance from the axis of rotation as the buoys.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
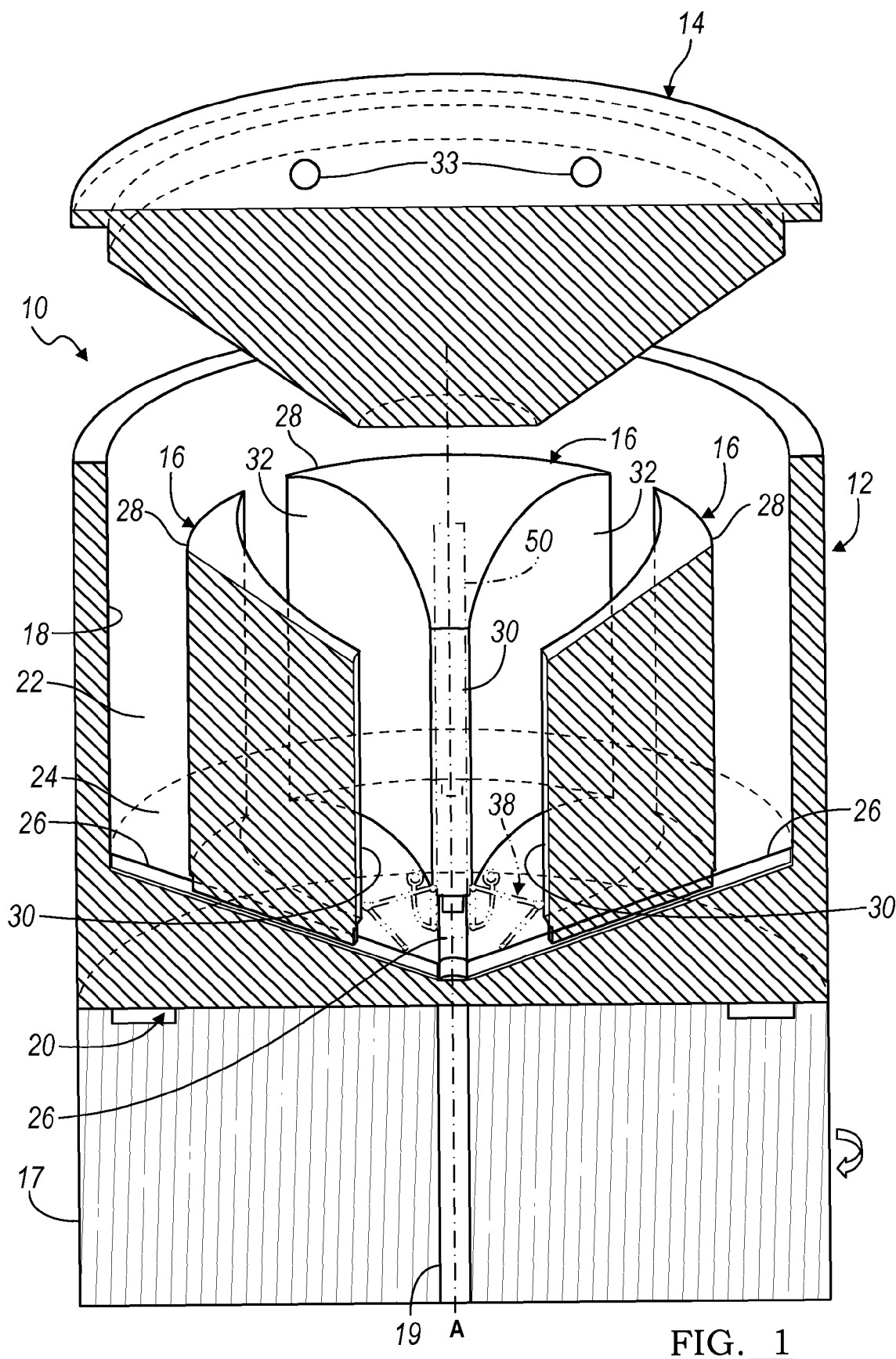
FIG. 1 is sectional side view of a separation device for separating components of a multi-component composition according to the present teachings.
Figure 2A:
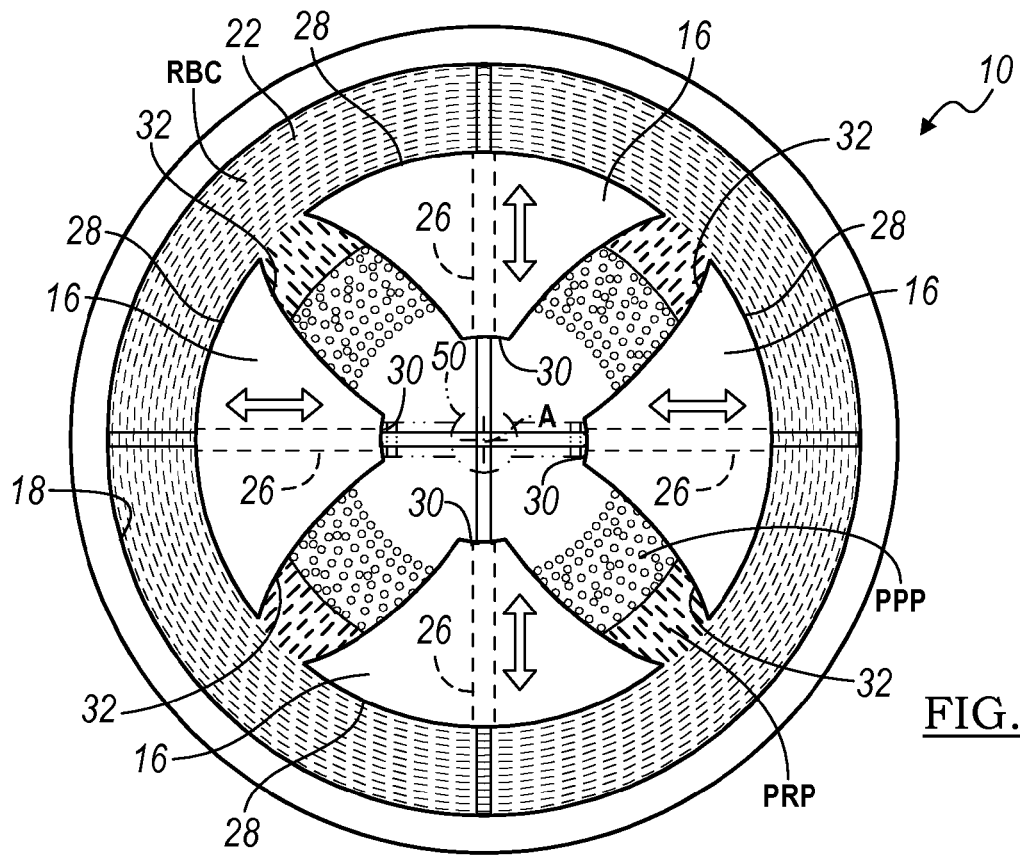
FIG. 2A is a top view of the device of FIG. 1 spinning on a rotating base, the device containing human whole blood.
Figure 2B:
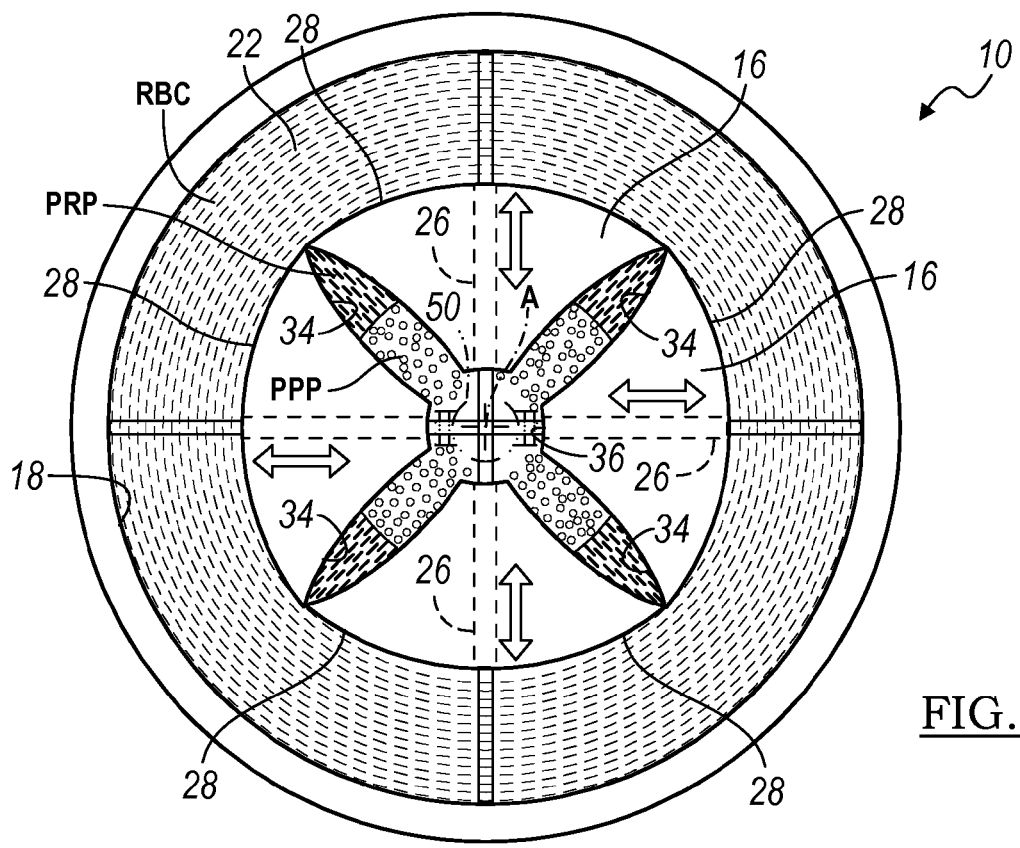
FIG. 2B is a top view of the device of FIG. 1 containing whole blood after it has been spun on a rotating base.

With initial reference to FIGS. 1, 2A, and 2B, a device for separating components of a multi-component composition according to the present teachings is illustrated at reference numeral 10. The device 10 generally includes a housing 12, a cover 14, and a plurality of buoys 16. The device 10 can be rotated or spun using a suitable rotating device 17, such as a Vortech® Base manufactured by Biomet, Inc. of Warsaw, Ind. (model nos. 800-7500A and 800-7600A, for example). The rotating device 17 can include any suitable mechanism for transferring torque from the rotating device 17 to the blood separation device 10, such as a rotating rod or spindle 19. The device 10 can be used to separate components of a variety of different compositions, such as whole blood, blood plasma, mononuclear cells ("MNC"), bone marrow aspirate, spinal fluid, and fat, for example.

The housing 12 includes a cylindrical sidewall 18 and a base 20. The cylindrical sidewall 18 defines a chamber 22. At the center of the chamber 22 is an axis of rotation A that extends longitudinally through the chamber 22. The device 10 rotates about the axis of rotation A when the device 10 is spun on the rotating device 17. The device 10 can include any suitable interface mechanism to permit the device 10 to cooperate with, and be rotated by, the rotating device 17.

The base 20 includes an inclined floor 24. The floor 24 is inclined from the axis of rotation A to the cylindrical sidewall 18. The floor 24 can be inclined at any suitable angle that is less than 90°, such as any suitable angle between about 15° and about 45°, such as about 25°. The floor 24 is inclined at this angle to cause the buoys 16 to move toward the axis of rotation A when the housing 12 is stationary.

The floor 24 includes a plurality of guide tracks 26. The guide tracks 26 extend generally from the axis of rotation A to the cylindrical sidewall 18. The guide tracks 26 can take the form of any suitable device capable of retaining the buoys 16 and permitting the buoys 16 to slide along the inclined floor 24 between the axis of rotation A and the cylindrical sidewall 18. For example, the guide tracks 26 can be rails recessed in, or protruding from, the inclined floor 24.

Each one of the buoys 16 is tapered such that an outer surface 28 of each buoy 16 proximate the cylindrical sidewall 18 has a larger surface area than an inner surface 30, which is proximate the axis of rotation A and distal to the cylindrical sidewall 18. Each buoy 16 includes side surfaces 32 that extend from the ends of the outer surface 28 to the inner surface 30. The outer, inner, and side surfaces 28, 30, and 32 can be of any suitable shape. As illustrated, the outer surfaces 28 are arcuate, the inner surfaces 30 are arcuate, and the side surfaces 32 are arcuate so as to be curved inward or hemispherical. Each buoy 16 is slidably mounted to one of the guide tracks 26 to permit each buoy 16 to slide along the inclined floor 24 and move radially inward and outward between the cylindrical sidewall 18 and the axis of rotation A. The buoys 16 are positioned about the axis of rotation A so as to surround the axis of rotation A.

The buoys 16 are movable between an expanded position (FIGS. 1 and 2A) and a contracted position (FIG. 2B), as further described herein. With additional reference to FIG. 3A, prior to initial rotation of the device 10, the buoys 16 are supported in the expanded position by support arms 38 (for clarity, FIGS. 1, 2A, and 2B do not illustrate the support arms 38). One support arm 38 is provided for each of the buoys 16. Each support arm 38 includes a first end 40 mounted to the inclined floor 24 and a second end 42 mounted to a slidable cylinder 44. The slidable cylinder 44 is mounted to a center post 50 that extends along the axis of rotation A. Between the first end 40 and the second end 42 is a hinged elbow portion 46. Weights 48 are also mounted to the slidable cylinder 44 with a hinge.

Figure 3A:
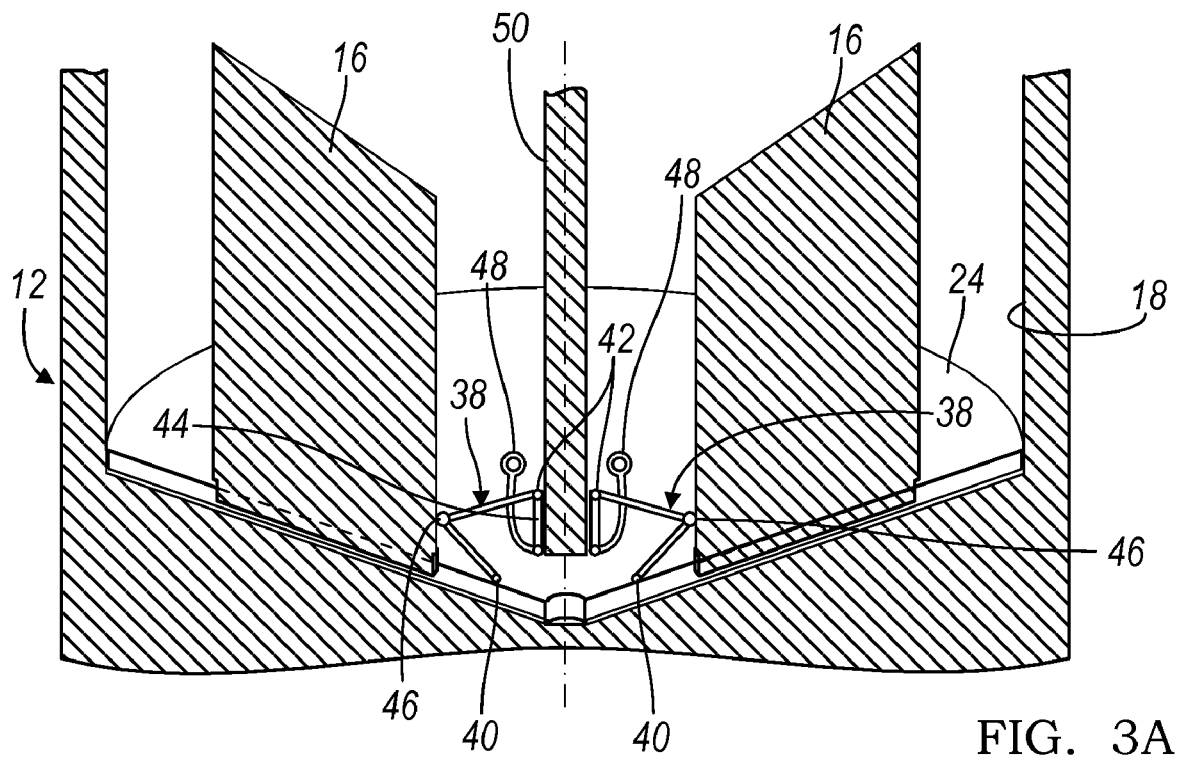
FIG. 3A is an expanded view of support arms of the device of FIG. 1, the support arms in a first position.

Before the housing 12 is initially rotated by the rotating device 17, the elbow portions 46 of the support arms 38 are in an extended position in which they contact the buoys 16 to support the buoys 16 in the expanded position of FIGS. 1, 2A, and 3A. Rotation of the device 10 results in movement of the weights 48 outward from the axis of rotation A towards the cylindrical sidewall 18 and the floor 24 of the chamber 22. As the weights move, the cylinder 44 moves away from the floor 24 along the axis of rotation A and the elbow portions 46 move inward toward the axis of rotation A to permit the buoys 16 to move to the retracted position. The cylinder 44 remains in the raised position of FIG. 3B after rotation of the chamber 22 is stopped, thereby permitting the buoys 16 to settle in the retracted position.

Each buoy 16 can be made of any appropriate material that may have a desired density. For example, when the device 10 is for separating blood, the buoys 16 can generally have a density that permits the buoys 16 to float on RBCs and find interface between RBCs and a PRP buffy coat or MNC fraction. For example, each buoy can have a density of generally between about 1.06 b/cc and about 1.11 g/cc. Further, the buoys 16 can have a density that is approximately equal to, or slightly greater than, the density of platelet rich plasma. To achieve the selected density, the buoys 16 can be formed of a single material or a composite having a plurality of materials. The density of the buoys 16 will also depend on the incline angle of the floor 24 as the angle will affect the position of the buoys 16. The angle of the floor 24 can be any suitable angle between about 15° and about 45°, such as about 25°, such that buoys 16 of a desired density will float on RBCs and find interface between RBCs and the PRP buffy coat or MNC fraction after blood within the device 10 has been spun for a suitable period of time.

The device 10 can be used to separate most any liquid composition into its constituent components by density. With particular reference to FIGS. 2A and 2B, operation of the device 10 to separate RBCs, PPP, and PRP from whole blood is described below.

Whole blood is loaded into the chamber 22 of the device 10 with the buoys 16 held in the expanded position by the elbow portion 46 of the support arms 38, as illustrated in FIGS. 1, 2A, and 3A. When the cover 14 is affixed to the chamber 22, the blood can be loaded through ports 33 in the cover 14. Alternatively, the cover 14 can be removed from the chamber 22 to permit blood to be loaded directly into the chamber 22.

The device 10 is spun using a suitable rotating mechanism, such as a Vortech Base. The device 10 is spun about its axis of rotation A. Rotation of the device 10 causes the hinged elbow portions 46 of the support arms 38 to move toward the axis of rotation A, as described above. However, rotation of the device 10 also causes the buoys 16 to remain in the expanded position even through the elbow portions 46 are no longer in contact with the buoys 16. Further, rotation of the device 10 causes separation of the different components of whole blood according to density.

Thus, as illustrated in FIG. 2A, as the component with the greatest density, RBCs gather at the outermost portion of the chamber 22, between the buoys 16 and the cylindrical sidewall 18. PRP, which is typically present in a buffy coat, gathers between the RBCs and the axis of rotation A in an area between two of the buoys 16. PPP, which is the least dense component, gathers near the axis of rotation A, interior to the RBCs and the PRP. Thus, the PRP gathers between the RBCs and the PPP.

Figure 3B:
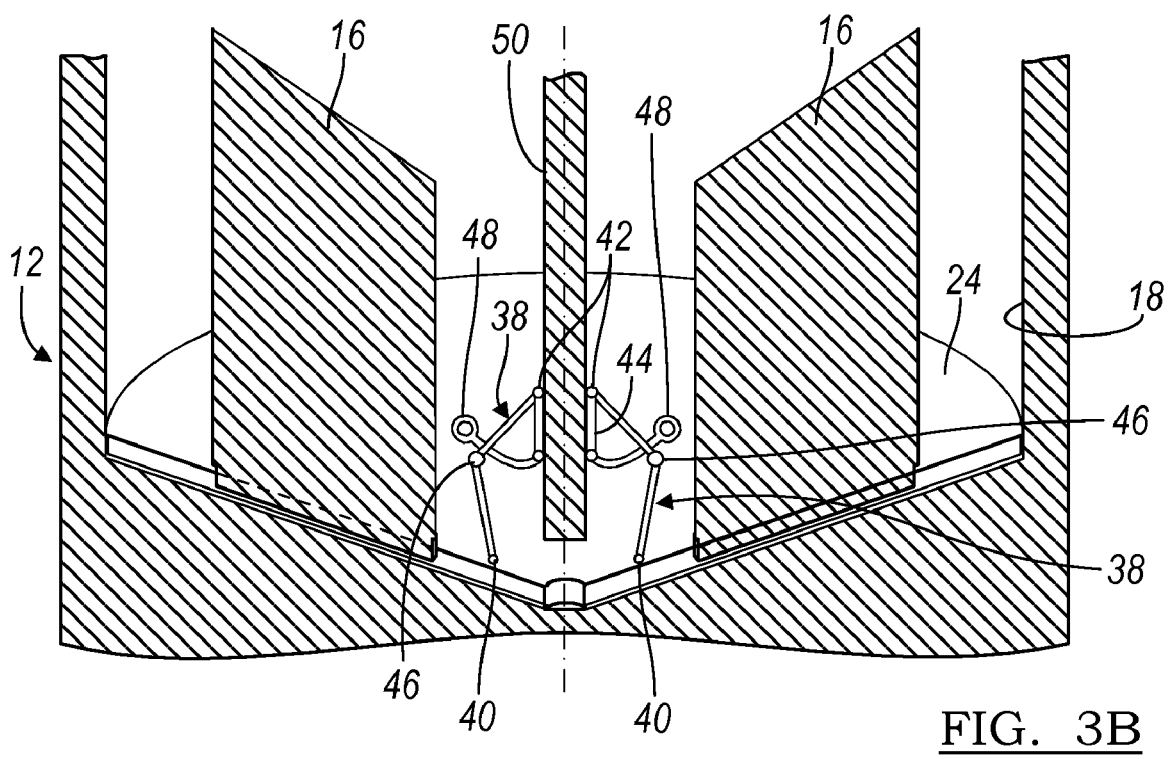
FIG. 3B is an expanded view of support arms of the device of FIG. 1, the support arms in a second position.

As illustrated in FIG. 2B, when the device 10 is stopped from rotating, the buoys 16 slide down the inclined floor 24 along the guide tracks 26 to move radially toward the axis of rotation A until the adjacent buoys 16 contact each other and settle in a contracted position. Movement of the buoys 16 to the contracted position is permitted because, as illustrated in FIG. 3B, the elbow portions 46 disengage the buoys 16 and move toward the axis of rotation A when the device 10 is rotated and remain in this position after the device 10 is stopped from rotating. Further, movement of the buoys 16 is facilitated by the inclined floor 24, which can be angled at from about 15° to about 45°, such as about 25° from the cylindrical sidewall 18 to the axis of rotation A. In the contracted position, adjacent buoys 16 only contact each other at their outer surface 28 to form a cylindrical wall about an exterior of the buoys 16. Because the side surfaces 32 are curved inward, the side surfaces 32 of adjacent buoys 16 do not contact each other. Instead, the side surfaces 32 of adjacent buoys 16 define pockets 34 between the buoys 16 when the buoys 16 are in the contracted position of FIG. 2B.

The majority of the PRP and the PPP is isolated in the pockets 34 after the device 10 is spun for a suitable period of time. The PRP is isolated at an outer portion of each pocket 34, proximate to the cylindrical sidewall 18. The PPP is isolated at an inner portion of each pocket 34, proximate the axis of rotation A. At least some of the isolated PPP can also gather in an interior chamber 36 formed between the buoys 16 at the axis of rotation and proximately surrounding the axis of rotation A. The interior chamber 36 is partially defined by the inner surface 30 of each buoy 16 and has a generally cylindrical shape. The majority of the RBCs are isolated between the contracted buoys 16 and the cylindrical sidewall 18.

The isolated RBCs, PRP, and PPP can be extracted from the device in any suitable manner using any suitable device. For example, the cover 14 can be removed and a select amount of RBCs, PRP, and/or PPP can be extracted using a syringe. The extracted RBCs, PRP, and/or PPP can be used for any suitable biological application.

Figure 4:
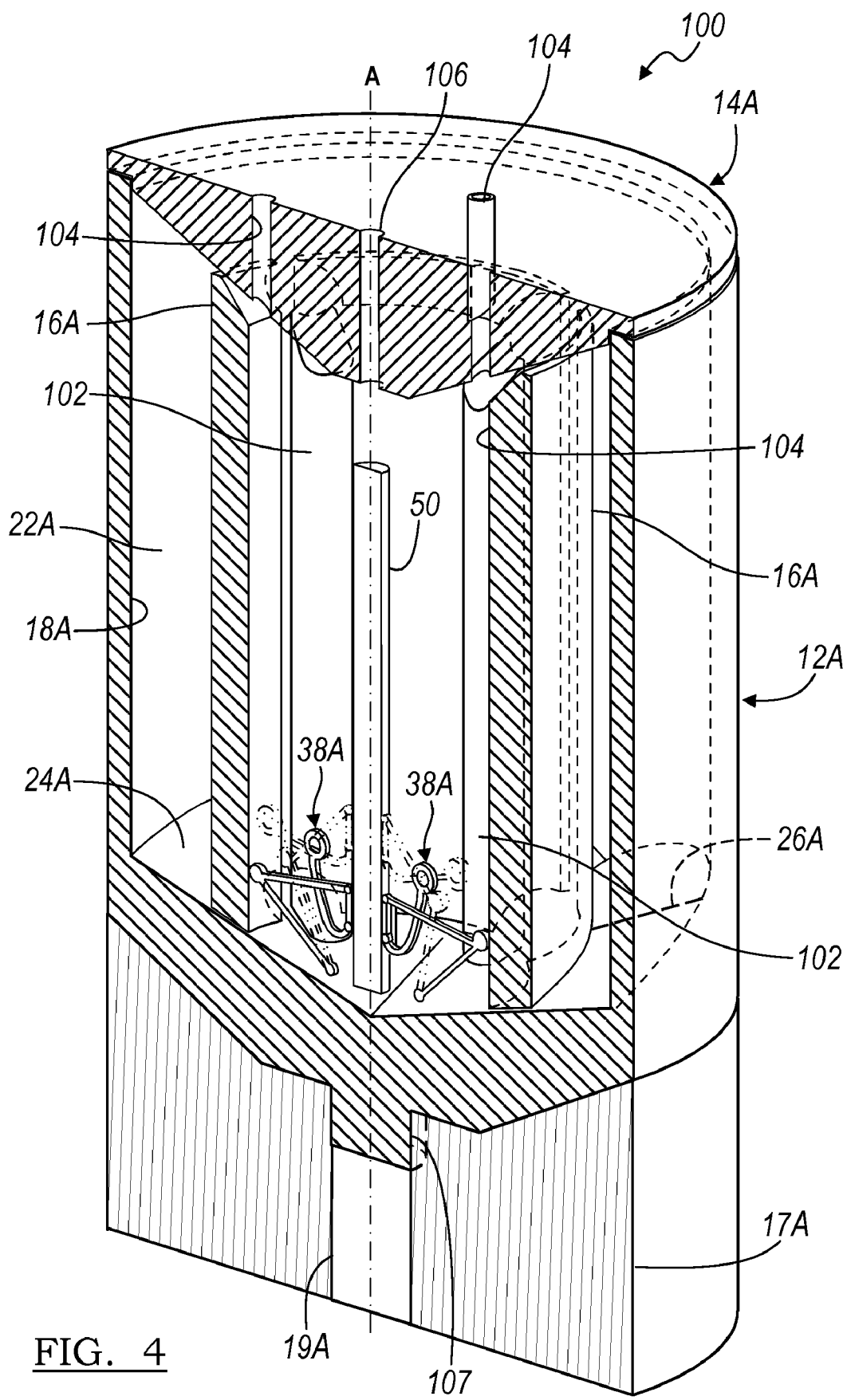
FIG. 4 is a sectional side view of a another blood separation device according to the present teachings.
Figure 5A:
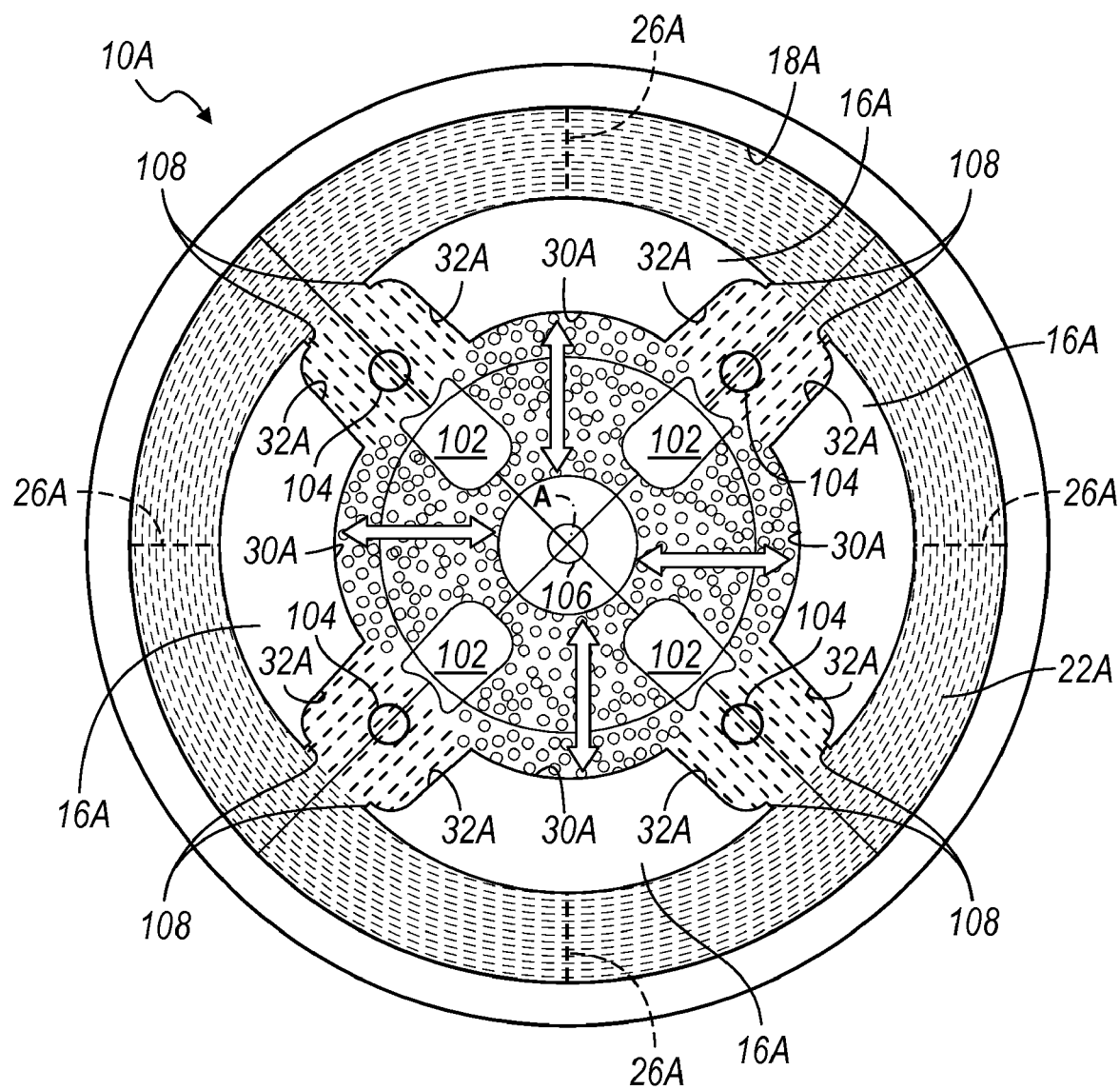
FIG. 5A is a top view of the device of FIG. 4 spinning on a rotating base, the device containing human whole blood.
Figure 5B:
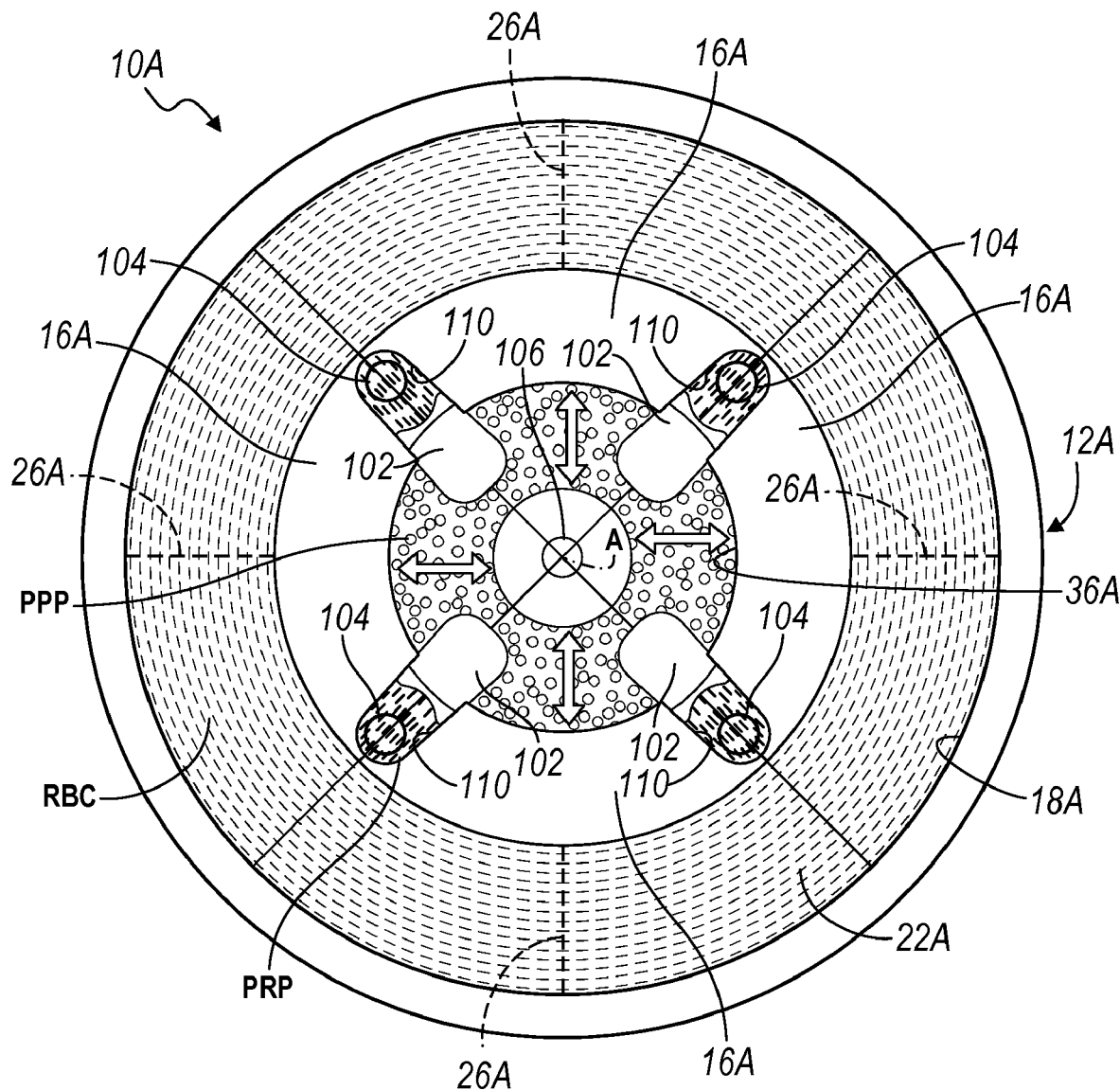
FIG. 5B is a top view of the device of FIG. 4 containing whole blood after it has been spun on a rotating base.
Figure 6:
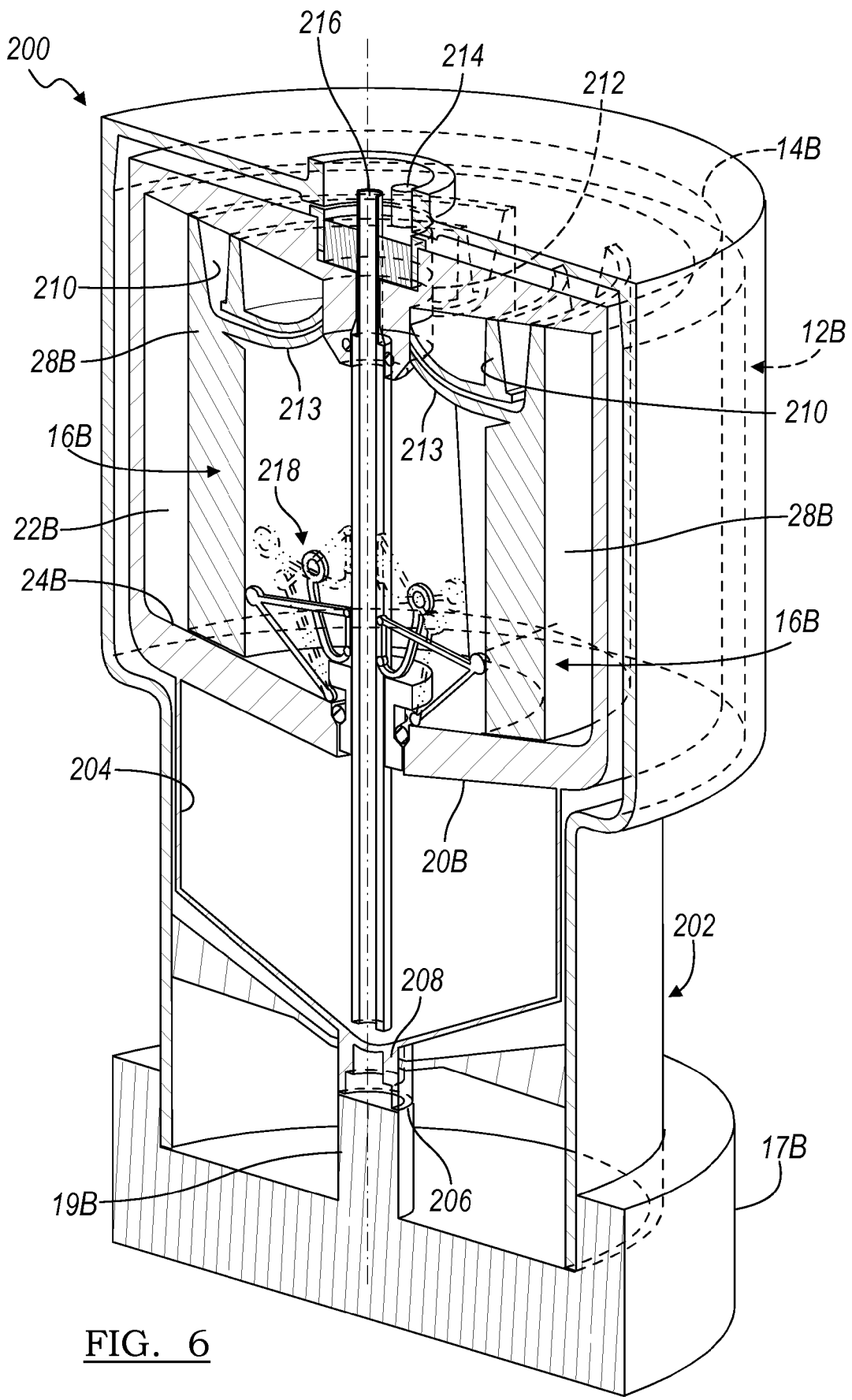
FIG. 6 is a sectional side view of another blood separation device according to the present teachings.

With reference to FIGS. 4, 5A, and 5B, a blood separation device 100 is illustrated. Features of the blood separation device 100 that are similar to the features of the blood separation device 10 are illustrated with like reference numbers, but also including the letter "A." With respect to these similar features, the above description of the device 10 also applies to the device 100.

The device 100 further includes stop posts 102, PRP withdrawal ports 104, PPP withdrawal ports 106, and an interface 107 for cooperating with a suitable rotational device, such as a Vortech Base (model numbers 800-7500A and 800-7600A) manufactured by Biomet Biologics of Warsaw, Ind.

The posts 102 are positioned about the axis of rotation A between the buoys 16A. The posts 102 generally extend from the inclined floor 24A to an upper surface of the cylindrical sidewall 18A, proximate to the cover 14A when it is in place over the chamber 22A. The buoys 16A include side tabs 108 that extend from the side surfaces 32A of the buoys 16A. The side surfaces 32A are generally planar. As illustrated in FIG. 5B, in the contracted position the side tabs 108 of adjacent buoys 16A contact each other and a portion of the side surfaces 32A opposite to the side tabs 108 contacts the posts 102 to form a pocket 110 between adjacent buoys 16A and the posts 102. After whole blood is spun for a suitable period of time and the buoys 16 have moved to the contacted position (FIG. 5B) from the expanded position (FIG. 5A) after rotation of the device 10, PRP is isolated in the pockets 110, isolated PPP gathers in the interior chamber 36A, and isolated RBCs gather between the buoys 16A and the cylindrical sidewall 18A.

The PRP withdrawal ports 104 are elongated tubes through which PRP can flow. The PRP withdrawal ports 104 are located in the pockets 110. The PRP withdrawal ports 104 have a distal end proximate to the inclined floor 24 and a proximal end that mates with the cover 14A when the cover 14A is in place over the chamber 22A. The PRP withdrawal port 104 extends through the cover 14. The PRP can be withdrawn through the ports 104 using any suitable extraction device, such as a syringe.

The PPP withdrawal port 106 is located within the interior chamber 36A, at or proximate to the axis of rotation A. The PPP withdrawal port 106 has a distal end proximate to the inclined floor 24 and a proximal end that mates with the cover 14A when the cover 14A is in place over the chamber 22A. The PPP withdrawal port 106 extends through the cover 14. The PPP can be withdrawn through the port 106 using any suitable extraction device, such as a syringe.

With reference to FIGS. 6, 7A, 7B, 8A, and 8B a blood separation device 200 is illustrated. Features of the blood separation device 200 that are similar to the features of the blood separation device 10 are illustrated with like reference numbers, but also including the letter "B". With respect to these similar features, the above description of the device 10 also applies to the device 200.

The device 200 further includes a casing 202 and a collection basin 204. The casing 202 surrounds the housing 12B and the collection basin 204. The casing 202 includes an interface 206 that can rotationally receive the collection basin 204 and a rotating device, such as the rotating rod 19B of the rotating device 17B. The interface 206 can transfer rotational torque generated by the rotating device to the collection basin 204 and the chamber 22B. The collection basin 204 extends from the base 20B of the device 200. The collection basin 204 includes a fitting 208 that is rotationally received within the interface 206.

The device 200 further includes PRP collection troughs 210. The troughs 210 are open at the sidewalls 32B, which are generally planar. The troughs 210 are present in the buoys 16B at an upper surface of each buoy 16B. The troughs 210 are in fluid communication with a central PRP collection bowl 212. The collection bowl 212 is located at a central portion of the chamber 22B at the axis of rotation A. The troughs 210 are in fluid communication with the collection bowl 212 by way of fluid lines 213 that extend between each trough 210 and the collection bowl 212. A PRP outlet port 214 extends from the collection bowl 212 to an exterior of the device through the cover 14B and through the casing 202.

The device 200 includes a PPP withdrawal port 216. The PPP withdrawal port 216 extends along the axis of rotation A. The withdrawal port 216 includes a distal end located in the collection basin 204 and proximal end that protrudes from the housing 12 and extends through the cover 14B and the casing 202.

Figure 8A:
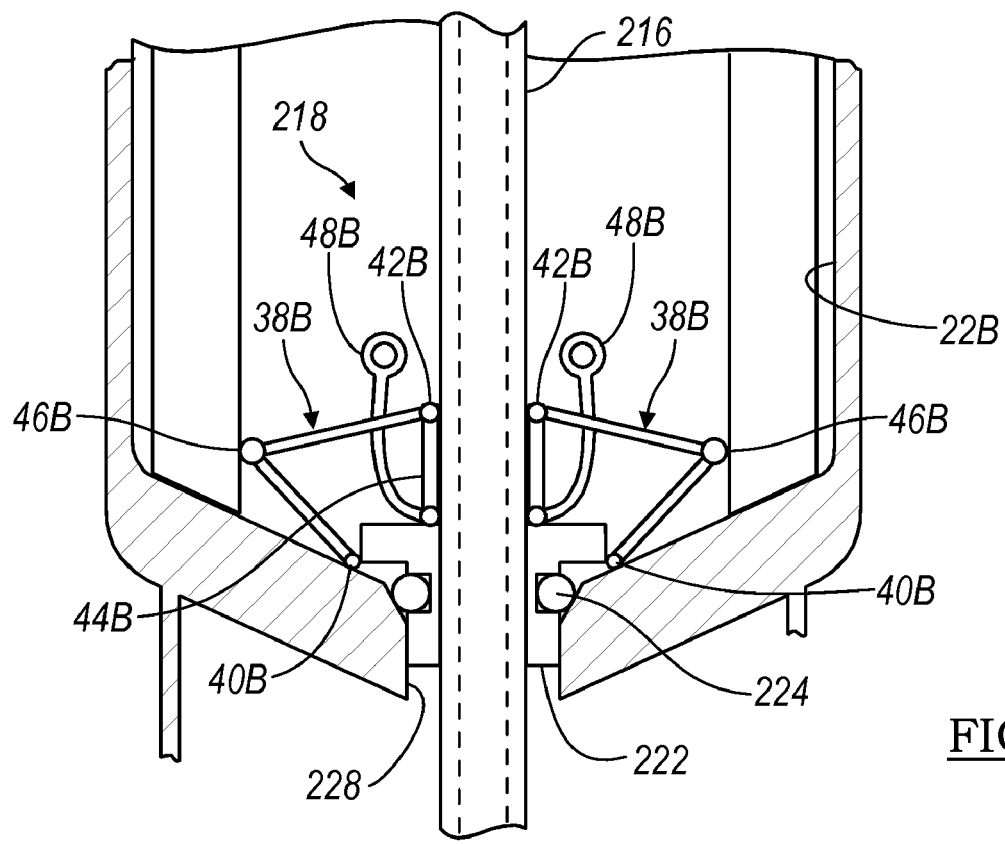
FIG. 8A is an expanded view of a valve of the device of FIG. 6, the device in a stationary position and the valve in a lowered position.
Figure 8B:
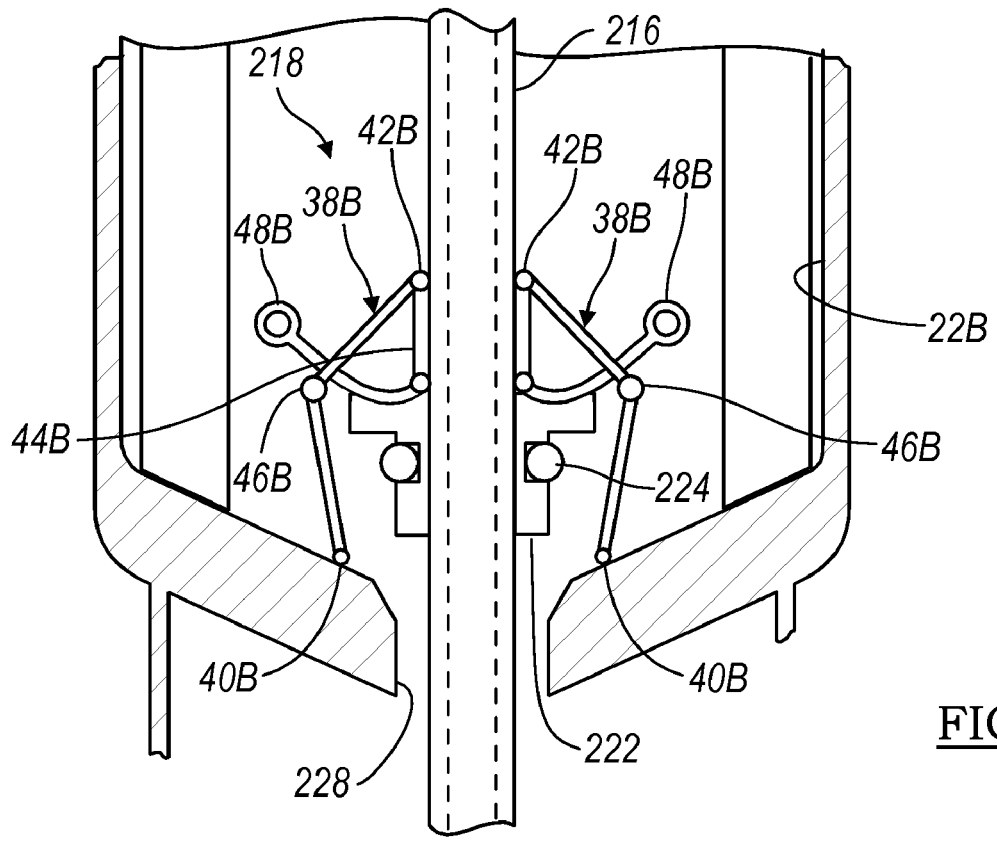
FIG. 8B is an expanded view of the valve of FIG. 6, the device in a rotating position and the valve in a raised position.

With additional reference to FIGS. 8A and 8B, the device 200 includes a valve 218. The valve 218 can be any suitable valve, such as the valve described in U.S. Patent Publication No. 2006/0175244 assigned to Hanuman LLC and Cell Factor Technologies, Inc. (filed Jan. 30, 2006; application Ser. No. 11/342,749), which is hereby incorporated by reference. The valve 218 includes a plug 222. The plug 222 is mounted to the cylinder 44B. The plug 222 includes a seal 224 that extends around an exterior of the plug 222. The seal 224 can be any suitable device or material that prevents the passage of materials. Also mounted to the cylinder 44B are the support arms 38B.

The plug 222 and the cylinder 44B are slidably mounted to the PPP port 216 at the axis of rotation A. The plug 222 is mounted such that it extends around the PPP port 216 and can slide up and down along the PPP port 216 between a lowered position (FIG. 8A) and a raised position (FIG. 8B). In the lowered position, the plug 222 is seated within an opening 228 of the inclined floor 24B, which surrounds the PPP port 216. In the raised position, the weights 48B extend outward toward the cylindrical sidewall 18B to raise the plug 222 out from within the opening to permit the passage of materials from the chamber 22B to the collection basin 204.

Figure 7A:
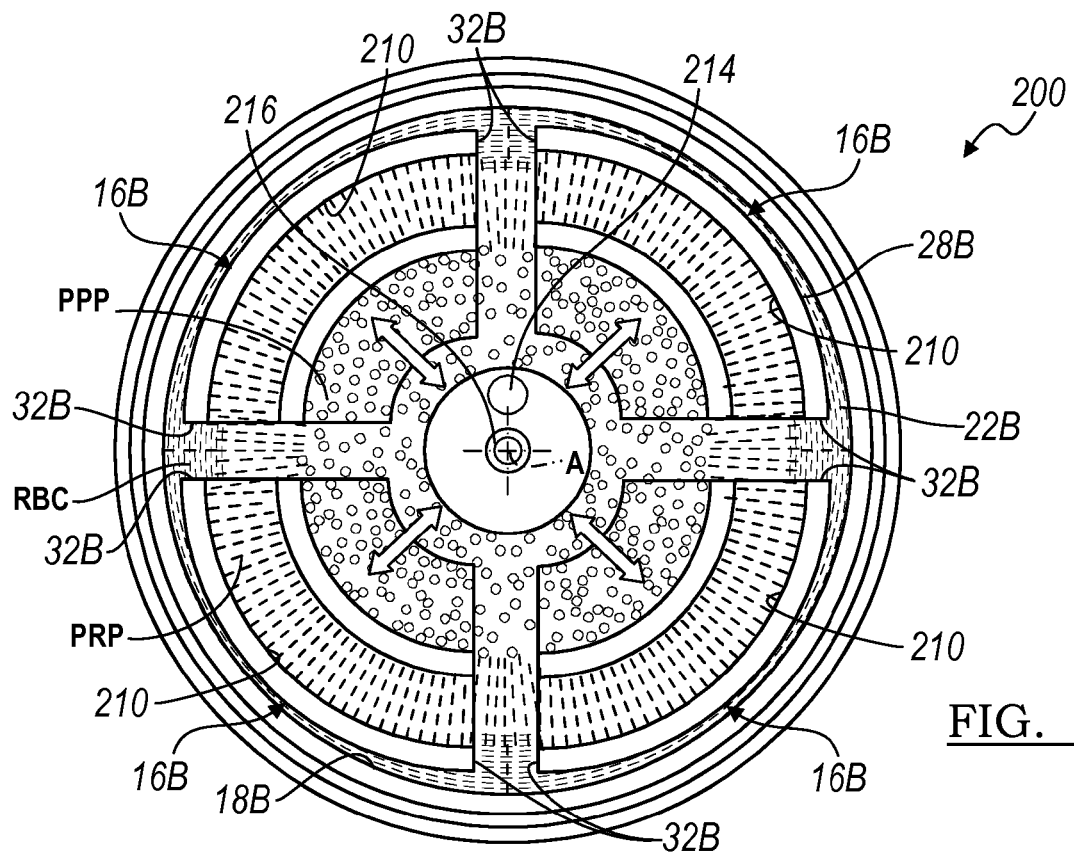
FIG. 7A is a top view of the device of FIG. 6 spinning on a rotating base, the device containing human whole blood.

In operation, a suitable rotating device, such as the rotating device 17A, is connected to the interface 206 to rotate the device 200 and the collection basin 204. As illustrated in FIG. 7A, rotating the device causes the components of whole blood to separate by density such that the RBCs are isolated between the cylindrical sidewall 18B and the buoys 16B, PRP is isolated in the collection troughs 210 of the buoys 16B, and PPP is isolated in the interior chamber 36B between the buoys 16B and the axis of rotation A. Rotating the device 200 further causes the plug 222 to move from the lowered position of FIG. 8A to the raised position of FIG. 8B and out from within the opening 228 to permit PPP within the interior chamber 36B to pass through the opening 228 into the collection basin 204.

Figure 7B:
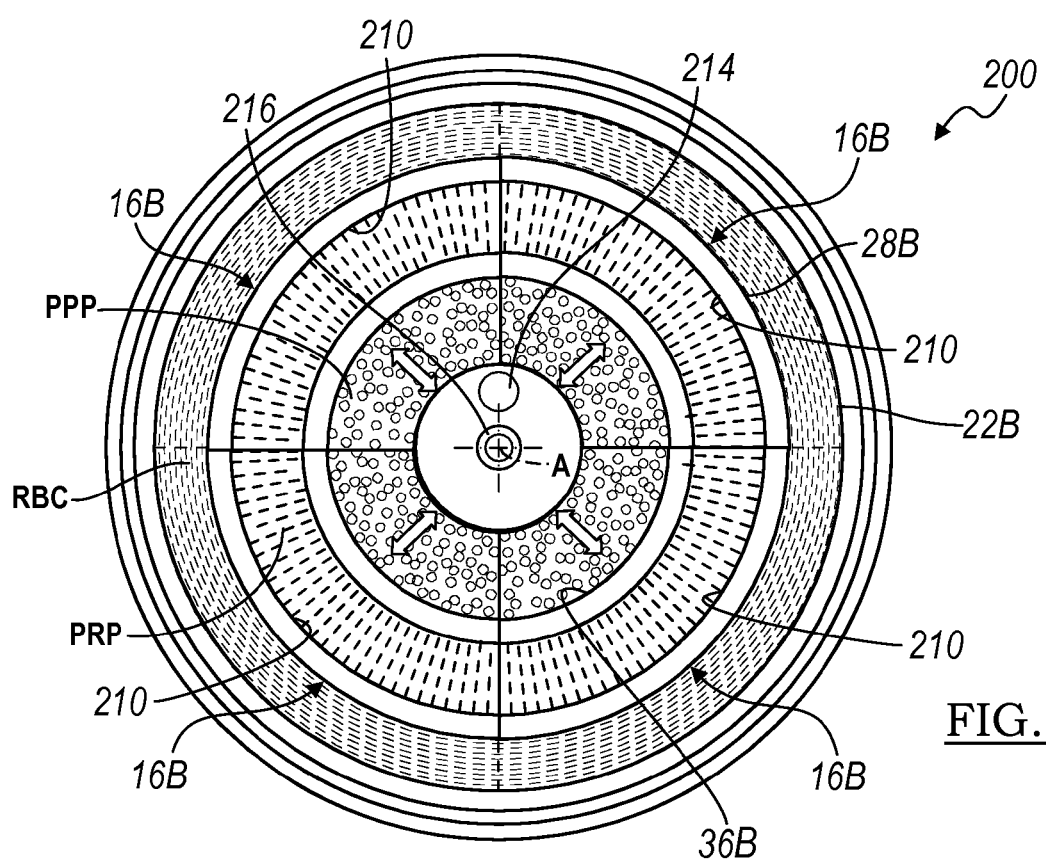
FIG. 7B is a top view of the device of FIG. 6 containing whole blood after it has been spun on a rotating base.

After the device 200 is spun, the buoys 16B move radially toward the axis of rotation A to isolate the PPP at the interior chamber 36B, the PRP in the collection troughs 210, and the RBCs between the outer surfaces 28B of the buoys 16B and the cylindrical sidewall 18B, as illustrated in FIG. 7B. The PRP can be removed via the PRP outlet port 214 using a suitable extraction device, such as a syringe. Using a syringe connected to the outlet port 214, PRP can be extracted from within the collection trough 210 by way of the fluid lines 213. PPP can be extracted from within the basin 204 by way of the PPP withdrawal port 216 using a suitable extraction device, such as a syringe. To facilitate removal of water from the PPP, dessicating beads can be provided within the collection basin 204.

Each device 10, 100, and 200 can also be used to separate components of bone marrow aspirate. For example, bone marrow aspirate can be obtained using any suitable bone marrow aspiration needle. To obtain bone marrow aspirate for separation, the bone marrow aspiration needle is advanced into the bone cortex and ultimately into the bone marrow cavity from where the bone marrow aspirate is withdrawn, typically using a syringe connected to the bone marrow aspiration needle. Any suitable amount of bone marrow aspirate can be used, such as about 300 cc, about 60 cc, or less than 60 cc. A suitable anticoagulant in a suitable amount is added to the bone marrow aspirate after it has been withdrawn from the bone marrow cavity.

When using the device 10 to isolate multipotent cells from bone marrow aspirate, the buoys 16 are set to a density that is approximate to, or slightly greater than, the density of the multipotent cells. This will allow the multipotent cells to be captured in the pockets 34. For example, the density of the buoys 16 can be about 1.08 g/cc to about 1.11 g/cc.

When using the device 10 to separate the components of bone marrow aspirate, the bone marrow aspirate is loaded into the chamber device 10 in the same manner that blood is. The device is then rotated according to the above description for separating blood components. After rotation and after the buoys move to the contracted position, the bone marrow aspirate is separated such that bone marrow plasma is isolated in a first capture area between the inner surface of the buoys 30 and the axis of rotation A. The heavy components of the bone marrow aspirate, such as the RBCs, are isolated in a second capture area between the cylindrical sidewall 18 and the outer surface 28 of the buoys 16. The multipotent cells are isolated in a third capture area that includes the pockets 34. The third capture area is between the first capture area and the second capture area. The different components of bone marrow aspirate can be removed in the same manner described above with respect to the different blood components.

While only the device 200 is illustrated as having the collection basin 204, the devices 10 and 100 can also include the collection basin 204 and the valve 218. Further, while only the device 100 is illustrated as including the ports 104 and 106, the ports 104 and 106 can be included in the device 10.

While devices 10, 100, and 200 each include four buoys 16, each device can include any suitable number of buoys 16. For example, the devices 10, 100, and 200 can include more than four buoys 16 and as few as one, two, or three buoys 16. Regardless of the number of buoys 16 provided, the buoys 16 can generally move radially along the inclined floor 24 between a contracted position in which the buoys 16 are proximate to the axis of rotation A and an expanded position in which the buoys 16 are distal to the axis of rotation A.

The devices 10, 100, and 200 can be used to isolate most any liquid composition into its constituent components by density. In order to adapt the devices 10, 100, and 200 to be used to separate different fluids, the density of the buoys 16 can be modified to approximate, or be slightly greater than, the density of the particular fluid component to be isolated, such that the buoys 16 will float on or find equilibrium in the rotating chamber 22 with the component to be isolated.

The description of the invention is merely exemplary in nature and, thus, variations that do not depart from the gist of the invention are intended to be within the scope of the inven-

What is claimed is:

1. A method for separating whole blood into different components comprising:
    inserting whole blood into a rotatable chamber of a blood separation device having an axis of rotation, an inner wall surface, and a plurality of movable buoys between the axis of rotation and the inner wall surface;
    rotating the chamber for a sufficient period of time such that components of the whole blood separate according to density; and
    stopping rotation of the chamber such that the plurality of buoys move from an expanded position in which the buoys are distal to the axis of rotation to a contracted position in which the buoys are proximal to the axis of rotation to isolate red blood cells of the blood between the buoys and the inner wall surface, to isolate platelet poor plasma between the buoys and the axis of rotation, and to isolate platelet rich plasma at a common distance from the axis of rotation as the buoys.

2. The method of claim 1, further comprising moving the buoys radially along an angled floor between the axis of rotation and the inner wall surface; wherein the floor is inclined from the axis of rotation to the inner wall surface.

3. The method of claim 1, further comprising collecting the platelet rich plasma in troughs formed in the buoys; and
    further comprising collecting the platelet rich plasma in the troughs in a collection bowl at the axis of rotation using fluid lines that extend between the troughs and the collection bowl.

4. The method of claim 1, further comprising collecting the platelet poor plasma in a collection basin attached to a bottom surface of the chamber; and regulating passage of the platelet poor plasma between the collection basin and the chamber with a valve.

5. A method for separating bone marrow aspirate into different components comprising:
    inserting bone marrow aspirate into a rotatable chamber of a bone marrow separation device having an axis of rotation, an inner wall surface, and a plurality of movable buoys between the axis of rotation and the inner wall surface;
    rotating the chamber for a sufficient period of time such that components of the bone marrow aspirate separate according to density; and
    stopping rotation of the chamber such that the plurality of buoys move from an expanded position in which the buoys are distal to the axis of rotation to a contracted position in which the buoys are proximal to the axis of rotation to isolate red blood cells of the bone marrow aspirate between the buoys and the inner wall surface, to isolate bone marrow plasma between the buoys and the axis of rotation, and to isolate multipotent cells at a common distance from the axis of rotation as the buoys.

6. The method of claim 5, further comprising moving the buoys radially along an angled floor between the axis of rotation and the inner wall surface; wherein the floor is inclined from the axis of rotation to the inner wall surface.

7. The method of claim 5, further comprising collecting the multipotent cells in troughs formed in the buoys; and
    further comprising collecting the multipotent cells in the troughs in a collection bowl at the axis of rotation using fluid lines that extend between the troughs and the collection bowl.

8. A method for separating components of a multi-component biological mixture comprising:
    inserting the mixture into a rotatable chamber of a separation device including an axis of rotation, an inner wall surface, and a plurality of movable buoys between the axis of rotation and the inner wall surface;
    rotating the chamber for a sufficient period of time such that components of the mixture separate according to density; and
    stopping rotation of the chamber such that the plurality of buoys move from an expanded position in which the buoys are distal to the axis of rotation to a contracted position in which the buoys are proximal to the axis of rotation to isolate a first component of the mixture between the buoys and the inner wall surface, to isolate a second component of the mixture between the buoys and the axis of rotation, and to isolate a third component of the mixture at a common distance from the axis of rotation as the buoys.

9. The method of claim 8, further comprising rotating the chamber by placing the chamber on a modular, rotating base.

10. The method of claim 8, wherein prior to rotating the chamber the buoys are in the expanded position.

11. The method of claim 10, wherein the buoys are supported in the expanded position by support arms.

12. The method of claim 8, further comprising stopping rotation of the chamber such that the buoys move radially along an angled floor of the chamber that is between the inner wall surface and the axis of rotation;
    wherein the floor is inclined from the axis of rotation to the inner wall surface to form a concave angled floor.

13. The method of claim 12, further comprising stopping rotation of the chamber such that the buoys move along guide tracks at the angled floor.

14. The method of claim 12, wherein the floor is inclined at an angle in the range of about 15° to about 45°.

15. The method of claim 12, wherein the floor is inclined at about 25°.

16. The method of claim 8, further comprising stopping rotation of the chamber such that the buoys contact stop posts when in the contracted position.

17. The method of claim 8, further comprising stopping rotation of the chamber such that side tabs of opposing buoys contact each other when in the contracted position.

18. The method of claim 8, wherein inserting the multi-component biological mixture includes inserting bone marrow aspirate; and
    wherein the first component includes red blood cells, the second component includes bone marrow plasma, and the third component includes multipotent cells.

19. The method of claim 18, wherein the buoys have a density of about 1.08 g/cc to about 1.11 g/cc.

20. The method of claim 18, further comprising loading bone marrow aspirate into the rotatable chamber through cover ports in a cover of the rotatable chamber.

21. The method of claim 18, further comprising stopping rotation of the chamber such that multipotent cells are isolated in pockets defined by opposing sidewalls of neighboring buoys when the buoys are in the contracted position.

22. The method of claim 21, further comprising extracting the multipotent cells from the pockets through withdrawal ports located within the pockets.

23. The method of claim 18, further comprising collecting the multipotent cells in troughs formed in the buoys; and
    further comprising extracting the multipotent cells collected in the troughs into a collection bowl at the axis of rotation using fluid lines that provide communication between the troughs and the collection bowl.

24. The method of claim 18, further comprising stopping rotation of the chamber such that bone marrow plasma is isolated in at least one of a pocket defined by opposing sidewalls of neighboring buoys when the buoys are in the contracted position, and an area of the chamber between the axis of rotation and the buoys.

25. The method of claim 24, further comprising extracting the bone marrow plasma through a center port proximate to the axis of rotation.

26. The method of claim 18, further comprising collecting the bone marrow plasma in a collection basin attached to an undersurface of the chamber; and regulating passage of the bone marrow plasma between the collection basin and the chamber with a valve at a passageway that provides communication between the chamber and the collection basin.

27. The method of claim 18, further comprising extracting at least one of the red blood cells, the bone marrow plasma, and the multipotent cells from the chamber with a syringe.

28. The method of claim 8, wherein inserting the multicomponent biological mixture includes inserting whole blood; and
wherein the first component includes red blood cells, the second component includes platelet poor plasma, and the third component includes platelet rich plasma.

29. A method for separating bone marrow aspirate into different components comprising:
inserting the bone marrow aspirate mixture into a rotatable chamber of a separation device including an axis of rotation, an inner wall surface, and a plurality of buoys movable between the axis of rotation and the inner wall surface, the buoys are movable from an expanded position in which the buoys are distal to the axis of rotation to a contracted position in which the buoys are proximal to the axis of rotation, the bone marrow aspirate mixture is inserted with the buoys in the expanded position;
rotating the chamber with a rotating base for a sufficient period of time such that components of the mixture separate according to density; and
stopping rotation of the chamber such that the plurality of buoys move radially along an angled floor of the chamber that is between the axis of rotation and the inner wall surface, the floor is inclined from the axis of rotation to the inner wall surface, the buoys move radially from the expanded position to the contracted position in order to:
isolate red blood cells of the mixture between the buoys and the inner wall surface;
isolate bone marrow plasma between the buoys and the axis of rotation; and
isolate multipotent cells at a common distance from the axis of rotation as the buoys.

30. The method of claim 29, wherein prior to rotating the chamber the buoys are supported in the expanded position with support arms.

31. The method of claim 29, wherein the floor is inclined at an angle of about 25°.

32. The method of claim 29, wherein the buoys have a density of about 1.08 g/cc to about 1.11 g/cc.

33. The method of claim 29, further comprising stopping rotation of the chamber such that the multipotent cells are isolated in pockets defined by opposing sidewalls of neighboring buoys when the buoys are in the contracted position.

34. The method of claim 29, further comprising collecting the multipotent cells in troughs formed in the buoys and extracting the multipotent cells collected in the troughs into a collection bowl at the axis of rotation using fluid lines that provide communication between the troughs and the collection bowl.

35. The method of claim 29, further comprising extracting the bone marrow plasma through a center port proximate to the axis of rotation.

36. The method of claim 35, further comprising collecting the bone marrow plasma in a collection basin attached to an undersurface of the chamber; and regulating passage of the bone marrow plasma between the collection basin and the chamber with a valve at a passageway that provides communication between the chamber and the collection basin.

* * * * *

UNITED STATES PATENT AND TRADEMARK OFFICE
CERTIFICATE OF CORRECTION

| | | |
|---|---|---|
| PATENT NO. | : 8,012,077 B2 | Page 1 of 1 |
| APPLICATION NO. | : 12/126028 | |
| DATED | : September 6, 2011 | |
| INVENTOR(S) | : Jacy C. Hoeppner | |

It is certified that error appears in the above-identified patent and that said Letters Patent is hereby corrected as shown below:

Title Page No. (56), References Cited, Other Publications, pg. 4, col. 2, reference no. 12, "Appllications" should be --Applications--.

Column 3, line 12, after "of", delete "a".

Column 4, line 58, "b/cc" should be --g/cc--.

Column 5, line 23, "through" should be --though--.

Column 8, lines 33-34, "inner surface of the buoys 30" should be --inner surface 30 of the buoys 16--.

Signed and Sealed this
Third Day of January, 2012

David J. Kappos
*Director of the United States Patent and Trademark Office*